United States Patent [19]
Eoga et al.

[11] Patent Number: 5,939,091
[45] Date of Patent: Aug. 17, 1999

[54] METHOD FOR MAKING FAST-MELT TABLETS

[75] Inventors: Anthony B. Eoga, Boonton; Kirti H. Valia, Plainsboro, both of N.J.

[73] Assignee: Warner Lambert Company, Morris Plains, N.J.

[21] Appl. No.: 09/040,749

[22] Filed: Mar. 18, 1998

Related U.S. Application Data

[60] Provisional application No. 60/047,217, May 20, 1997.

[51] Int. Cl.$^6$ ........................................................ A61K 9/46
[52] U.S. Cl. .......................... 424/441; 424/464; 424/465; 424/466; 514/819
[58] Field of Search .................................... 424/464, 466, 424/465, 441; 514/819

[56] References Cited

U.S. PATENT DOCUMENTS

| | | |
|---|---|---|
| 4,371,516 | 2/1983 | Gregory et al. . |
| 4,507,511 | 3/1985 | Reiff et al. . |
| 4,650,669 | 3/1987 | Alexander et al. . |
| 4,684,534 | 8/1987 | Valentine . |
| 4,855,326 | 8/1989 | Fuisz . |
| 5,073,377 | 12/1991 | Alexander et al. . |
| 5,169,640 | 12/1992 | France et al. . |
| 5,178,878 | 1/1993 | Wehling et al. . |
| 5,244,670 | 9/1993 | Upson et al. . |
| 5,501,861 | 3/1996 | Makino et al. . |
| 5,562,919 | 10/1996 | Doty et al. . |
| 5,576,014 | 11/1996 | Mizumoto et al. . |
| 5,807,577 | 9/1998 | Ouali . |

FOREIGN PATENT DOCUMENTS

| | | |
|---|---|---|
| 1617638 | 5/1971 | Germany . |
| 39 27 398 | 2/1991 | Germany . |
| 1123336 | 8/1968 | United Kingdom . |
| 9300828 | 1/1993 | WIPO . |
| 9623494 | 8/1996 | WIPO . |

*Primary Examiner*—Thurman K. Page
*Assistant Examiner*—Brian K. Seidleck
*Attorney, Agent, or Firm*—Evan J. Federman

[57] ABSTRACT

A process for making a fast melt tablet and a powdered material is disclosed. The process includes providing a powdered material with a density of from 0.2 to about 0.55 grams and precompacting the material to increase the density prior to compacting the powdered material into a fast melt tablet.

20 Claims, No Drawings

METHOD FOR MAKING FAST-MELT TABLETS

This application claims the benefit of U.S. Provisional application Ser. No. 60/047,217, filed May 20, 1997.

BACKGROUND OF THE INVENTION

1. Field of the Invention

The present invention relates to intrabuccally dissolving and partially dissolving compressed tablets and a method for their manufacture. The tablets deliver an active ingredient in an easy chew form that quickly disintegrates in the buccal cavity. Particularly, the present invention relates to intrabuccally dissolving and disintegrating tablets comprised of low density granules prepared from inactive and/or active raw material ingredients. The tablets are useful in the pharmaceutical and confectionery fields. The low density granules are prepared from active and/or inactive raw material ingredients and low density ingredients such as alkali earth metal salts, water soluble carbohydrates and mixtures thereof. The present invention also comprises a process for the preparation of the low density granules, and a process for the preparation of tablets using the low density granules.

2. Description of Related Art

Compressed tablets are solid dosage forms prepared by compacting a formulation containing an active ingredient and excipients selected to aid the processing and improve the properties of the product. The term "compressed tablet" generally refers to a plain, uncoated tablet for oral ingestion, prepared by a single compression or by pre-compaction tapping followed by a final compression. Such pre-compaction tapping does not necessarily overcome the flow and die fill problems associated with the use of very fine particles prior to the final compression of the tablets.

Tablets can be made in many sizes and shapes, with a variety of properties. Tablets are the most widely used of all pharmaceutical dosage forms for a number of reasons. They are convenient, easy to use, and less expensive to manufacture than other oral dosage forms. They deliver the intended dose with a high degree of accuracy. A popular type of tablet that has been developed for special application is the buccal tablet.

Despite their benefits, buccal tablets have certain drawbacks. Foremost is the fact that buccal tablets dissolve slowly in the buccal pouch. In general, the hardness levels of compressed tablets are not adequate for fast disintegration in the buccal cavity and ultimately in the digestive tract through oral administration. This is especially disconcerting to those consumers unable to swallow or chew conventional compressed tablets.

Consequently, there is a great need for a tablet that rapidly dissolves and absorbs with sufficient speed so that the tablet can be used by consumers who otherwise do not use tablets. Others have recognized and worked on the problem. U.S. Pat. No. 4,855,326, describes a melt spinnable carrier agent such as sugar combined with a medicament that is converted into fiber form by melt spinning with "cotton candy" fabricating equipment. The as-spun product is converted to compacted individual dosage units that reportedly display rapid entry into solution upon contact with a solvent.

While the melt spinnable product confers advantageous properties amenable to consumers who are unable to swallow or chew conventional compressed tablets, they are not without certain disadvantages. Most critical is that the melt spinning step is required in addition to direct compression techniques. A procedure employing only direct compression is by far the desired method from the standpoint of processing procedures, equipment and materials.

U.S. Pat. No. 4,684,534 discloses tablets having a harder outer shell that inhibits penetration of liquid into the interior of the tablet. The interior of the tablet is softer and quickly liquifies when the shell is broken and the interior contacts liquid.

U.S. Pat. No. 5,178,878 discloses a tablet made from microparticles and an effervescent disintegration agent. When the tablet is taken orally, the effervescent disintegration agent aids in rapid dissolution of the tablet.

U.S. Pat. No. 5,501,861 discloses fast dissolving tablets. The tablets have a porosity of 30 to 70%, a hardness of 3 to 20 kg and a falling impact strength of 0 to 70%. The tablets are made with water-soluble carbohydrates and 1 to 3% by weight of water. The tablets are made by adhering particles of carbohydrate to each other by moistening the surfaces of the particles with the water, compressing the particles and removing the water.

U.S. Pat. No. 5,576,014 discloses an intrabuccally dissolving compressed molding made from a granulated saccharide having low moldability and a saccharide having high moldability. The blending ratio of the high moldability saccharide to the low moldability saccharide is 2 to 20% by weight. The moldings quickly disintegrate in the buccal cavity and have adequate hardness.

German Patent Document 1,617,638 teaches sorbitol for use as a tablet binder. The density of the sorbitol used is between 0.53 and 0.545 gms/cm$^3$.

SUMMARY OF THE INVENTION

The present invention provides a rapidly dissoluble dosage unit, such as a tablet, that can be employed in both the pharmaceutical and confectionery fields. The dosage unit quickly disintegrates and partially or totally dissolves in the buccal cavity. The tablet has a hardness sufficient to retain its dosage integrity or form and is still capable of being easily chewed.

The present invention also includes a process for preparing tablets by compacting granules that are made from one or more low density alkali earth metal salts, water soluble carbohydrates or mixtures thereof.

The low density alkali earth metal salts used in the granules include calcium carbonate, calcium hydroxide, magnesium carbonate, magnesium hydroxide, aluminum hydroxide, magnesium silicate, magnesium aluminate or aluminum magnesium hydroxide. The water soluble carbohydrates are preferably highly porous and can be selected from a high moldability or low moldability type. High moldability type, water soluble carbohydrates include maltose, maltitol and sorbitol. Low moldability type, water soluble carbohydrates include mannitol, glucose, sucrose and xylitol. The granules used to make the tablets according to the present invention can also be made from other raw materials including starches, proteins, maltodextrins and oligosaccharides. Additionally, there are many coated and uncoated drugs, other active ingredients, non-carbohydrate ingredients that are highly soluble in the buccal cavity and highly porous.

Although the direct use of higher density alkali earth metal salts and water soluble carbohydrates provide adequate tablet hardness levels, they do not provide for low density tablets that disintegrate quickly when chewed and have a smooth mouthfeel. Additionally, while the direct use of a low density alkali earth metal salt or water soluble carbohydrate provides for a smooth mouthfeel, it is also difficult to compress these ingredients because of their low density and fine mesh size. Although the spray drying of higher density alkali earth metal salts and water soluble carbohydrates provide adequate tablet hardness levels, they do not generally provide for low density tablets that exhibit quick disintegration in the buccal cavity and a smooth mouthfeel. Prior art spray dried tablet ingredients also exhibit a high mesh size profile (very fine particles) that does not always match the mesh size profile of a number of active and inactive ingredients. This could lead to inadequate content uniformity. However, when low density alkali earth metal salt or water soluble carbohydrate are either spray dried or pre-compacted, the resulting granules can be compressed to obtain structurally sound tablets that are easy to chew and quickly dissolve. Additionally, tablets made from the granules produce a low density product with optimal content uniformity.

The present invention includes fast chewing, rapidly dissolving tablets made from granules that are prepared from a variety of raw materials. The present invention also includes processes for preparing the granules. The granules can be prepared by either spray drying or pre-compacting the ingredients. When the granules are compressed into tablets with other excipients, the resulting tablets exhibit a low density, sufficient hardness to permit for easy chew characteristics, fast disintegration, smooth mouthfeel, and fast dissolution in the digestive tract. Other objects of the present invention will occur to those skilled in the subject art after reading the following detailed description.

DETAILED DESCRIPTION OF THE INVENTION

The granules used to make the tablets of the present invention are prepared from low density alkali earth metal salts, low density water soluble carbohydrates and mixtures thereof. The low density alkali earth metal salts of the present invention are known to those skilled in the art. Non-limiting examples of alkali earth metal salts include calcium carbonate, calcium hydroxide, magnesium carbonate, magnesium hydroxide, magnesium silicate, magnesium aluminate, aluminum hydroxide or aluminum magnesium hydroxide. A particular alkali earth metal salt useful for making an antacid tablet is calcium carbonate.

Water soluble low density carbohydrates of the present invention are known to those skilled in the art. The water soluble low density carbohydrates are preferably highly porous and can be selected from a high moldability or low moldability type. Preferably, the water soluble low density carbohydrate is one that has a quick disintegration and dissolution rate in the buccal cavity and a high moldability to give adequate hardness when produced by compression molding such as tableting. High moldability type water soluble carbohydrates are selected from the group consisting of maltose, maltitol and sorbitol. Low moldability type water soluble carbohydrates are selected from the group consisting of mannitol, glucose, sucrose and xylitol.

An example of a water soluble low density carbohydrate that exhibits adequate particle size distribution used to make the granules according to the present invention is Sorbitol Instant, available from E. M. Industries, Inc. Hawthorne, N.Y. Sorbitol Instant consists of very loosely packed randomly oriented, interwoven filamentary crystals. These crystals allow smaller sized drug substances to be entrapped in the filamentary matrix of the Sorbitol Instant crystals. The as is density of Sorbitol Instant, prior to being processed according to the present invention, is about 0.38 to about 0.46 gm/ml. The tapped density is about 0.45 to about 0.50 gm/ml. Sorbitol Instant can be used with and without low density alkali earth metal salts.

An example of a low density alkali earth metal salt useful for making the granules according to the present invention is extra light calcium carbonate available from Specialty Minerals Inc., Adams, Me. The density of the extra light calcium carbonate, prior to being processed according to the present invention, is about 0.37 gm/ml.

The granules used to make the tablets according to the present invention are made by either spray drying or pre-compacting the raw materials. Prior to being processed into granules by either process, the density of the alkali earth metal salts useful in the present invention ranges from about 0.3 grams/ml to about 0.55 grams/ml, preferably about 0.35 grams/ml to about 0.45 grams/ml, even more preferably about 0.37 grams/ml to about 0.42 grams/ml. The density of the carbohydrate depends upon the mesh size and the final process used to produce the carbohydrate The Spray Drying Process The spray drying process used to make the granules is a conventional process known to those skilled in the art. The raw materials are slurried in deionized water. The slurry is transferred into the spray dryer. The spray drying parameters can be adjusted depending upon the raw materials used. The spray drying of a calcium carbonate/modified starch blend is performed using an inlet temperature of 190° C. +/–5° C. and an outlet temperature of 100° C. +/–5° C. The final density of the material after spray drying will vary depending upon the process used to produce the product.

The Pre-compacting Process

The pre-compacting or pre-compressing process for making the granules can be accomplished by applying a force to the raw material. That is, the raw material is in the from of particles that have a low starting density. A low starting density is from about 0.1 grams/ml to about 1.0 grams/ml. The material is subjected to a compressive force that produces a material with a density higher than the starting density.

One method of applying the force is by processing the material in the Gerteis GMP Roller Compactor, available from Gerteis Macshinen, Jona, Switzerland. Another compactor useful in the pre-compressing process is a Chilsonator made by the Fitzpatrick Co., Elmhurst, Ill. The compactors work by feeding the powdered material through rollers.

There are five variables that can effect the density and uniformity of the compacted material when processed by the Gerteis machine. Specifically, the force speed, the gap between the rollers, the speed of the rollers, the speed of the oscillating granulator and the mesh size of the screen can be varied depending upon the properties of the raw material and the properties desired in the compacted material.

The compactor can be run at a force speed of from about 1.0 KN/Cm to about 9.0 KN/Cm, preferably about 1.0 KN/Cm to about 5.0 KN/Cm, even more preferably about 1.5 KN/Cm to about 2.5 KN/Cm. The gap between the rollers in the compactor is set between about 2 mm to about 6 mm. The roller speed is from about 4 rpm to about 8 rpm. The oscillator and the mesh screen can be adjusted to deliver the mesh size profile desired.

The density of the granules that result from either the spray drying or pre-compaction process will vary depending upon the density of the materials prior to processing. For example the density of an extra light calcium carbonate increased from 0.37 grams/ml to 0.41 grams/ml after pre-compaction. Both spray drying and pre-compaction increase the density of the particles sufficient to compress them into structurally sound tablets capable of rapid disintegration upon chewing. The pre-compressed raw materials are sized to obtain a specific mesh size profile that closely matches the mesh size profile of the other ingredients used in the tablet.

Tablet Preparation

The granules made by either the spray drying or pre-compacting processes are mixed with excipients and compressed into tablets using conventional tablet making machinery. The granules can be combined with a variety of carriers including low density, high moldability saccharides, low moldability saccharides, polyol combinations, and then directly compressed into a tablet that exhibits an improved dissolution and disintegration profile.

The tablets according to the present invention have a hardness of about 2 to about 6 scu. Tablets within this hardness range disintegrate or dissolve rapidly when chewed. Additionally, the tablets rapidly disentegrate in water. On average, a 1.1 to 1.5 gram tablet disintegrates in 1–3 minutes without stirring. This rapid disintegration facilitates delivery of the active material.

The granules used to make the tablets can be mixtures of low density alkali earth metal salts or carbohydrates. For example, a mixture of alkali earth metal salts includes a combination of calcium carbonate and magnesium hydroxide. Similarly, a tablet can be prepared according to the methods of the present invention that incorporates the use of A) spray dried extra light calcium carbonate/maltodextrin, B) magnesium hydroxide and C) a eutectic polyol combination including Sorbitol Instant, xylitol and mannitol. These materials have been combined to produce a low density tablet that dissolves very readily and promotes the fast disintegration of the active ingredient. Additionally, the pre-compacted and spray dried granules can be combined in the same tablet.

The tablets of the present invention optionally contain pharmaceutically active ingredients. An active ingredient useful in the present invention can be any form, such as solid, particulate, granular, crystalline, oily or solution. The active ingredient for use in the present invention may be a spray dried product or an adsorbate that has been pre-compacted to a harder granular form that reduces the medicament taste. A pharmaceutical active ingredient for use in the present invention may be spray dried with a carrier that prevents the active ingredient form being easily extracted from the tablet when chewed.

The active ingredient may be a medicament drug that is selected from a wide variety of drugs and their acid addition salts. Both organic and inorganic salts may be used provided the drug maintains its medicament value. The active ingredient may be at least one member selected from the group consisting of nourishing and health-promoting agents, antipyretic agents, analgesic agents, antiinflammatory agents (including NSAIDS), antipsychotic drugs, antianxiety drugs, antidepressants, hypnotic-sedative agents, spasmolytics, gastrointestinal agents (H1 or H2 receptor antagonists and proton pump inhibitors), antacids, antitussives, expectorants, antihistamines, cardiotonics, antiarrhythmic drugs, antiemetic, antinauseant, diuretics, antihypertensive drugs, vasoconstrictors, coronary vasodilators, antibiotics, vasodilators, chemotherapeutic drugs, antidiabetic agents, drugs for osteoporosis, skeletal muscle relaxants, and mixtures thereof.

In addition to being added to the tablets of the present invention, the medicament drug itself can be processed by the pre-compaction process to achieve an increased density prior to being incorporated into the formulation.

The pre-compaction process used in the present invention can be used to deliver poorly soluble pharmaceutical materials so as to improve the release of such pharmaceutical materials over traditional dosage forms. This could allow for the use of lower dosage levels to deliver equivalent bioavailable levels of drug and thereby lower toxicity levels of both currently marketed drug and new chemical entities. Poorly soluble pharmaceutical materials can be used in the form of nanoparticles, which are nanometer-sized particles.

In addition to the active ingredient and the granules prepared from low density alkali earth metal salts and/or water soluble carbohydrates, the tablets can be formulated using conventional carriers or excipients and well established pharmaceutical techniques. Conventional carriers or excipients include, but are not limited to, diluents, binders, adhesives (i.e., cellulose derivatives and acrylic derivatives), lubricants (i.e., magnesium or calcium stearate, vegetable oils, polyethylene glycols, talc, sodium lauryl sulphate, polyoxy ethylene monostearate), disintegrants, colorants, flavorings, preservatives, sweeteners and miscellaneous materials such as buffers and adsorbents.

In addition to tablets, the particles made by the process of the present invention can also be incorporated into aerosols, topical products, confections and chewing gums. The preparation of confectionery and chewing gum products is historically well known and has changed very little over the years. Thus, for example, the granules prepared from low density inactive ingredients may be combined with a binding agent (e.g., polyvinylpyrrolidone or hydroxypropyl methylcellulose) and other suitable excipients such as fillers (e.g., sugars such as lactose, sucrose, dextrose, fructose, maltose and mannose, preferably fructose and mannose, or sugar alcohols such as sorbitol, xylitol and mannitol). Tablets may be obtained by compressing the granules with suitable tabletting aids such as lubricants (e.g., magnesium stearate) and additional binder. Cast chewable tablets may be prepared by incorporating the granules in one or more low melting point fatty bases such as triglyceride bases.

Compressed tablet lozenges can also be prepared. In addition to the granules, they generally contain sugars in amounts up to 95% and typical tablet excipients such as binders and lubricants as well as flavors, colorants and so forth. The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7 gm/ml.

By comparison, the high boiling syrup, or "bob syrup", is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, CHOCOLATE, COCOA AND CONFECTIONERY: Science and Technology, 2nd edition, AVI Publishing Co., Inc., Westport, Conn., (1980), at Pages 424–425.

A general discussion of the lozenge and chewable tablet forms of confectionery may be found in H. A. Lieberman and L. Lachman, Pharmaceutical Dosage Forms: Tablets Volume 1, Marcel Dekker, Inc., New York, N.Y. at pages 289 to 466.

In the instance where auxiliary sweeteners are utilized, the present invention contemplates the inclusion of those sweeteners well known in the art, including both natural and artificial sweeteners. Thus, additional sweeteners may include, among others, water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof; water-soluble artificial sweeteners such as the soluble saccharin salts, i.e., sodium, or calcium saccharin salts, cyclamate salts, acesulfam-K and the like, and the free acid form of saccharin and dipeptide based sweeteners such as L-aspartyl-phenylalanine methyl ester and materials described in U.S. Pat. No. 3,492,131 and the like.

In general, the amount of sweetener will vary with the desired amount of sweeteners selected for a particular tablet composition.

Suitable flavorings include both natural and artificial flavors, and mints such as peppermint, menthol, artificial vanilla, cinnamon, various fruit flavors, both individual and mixed, essential oils (i.e. thymol, eculyptol, menthol and methyl salicylate) and the like are contemplated. The flavorings are generally utilized in amounts that will vary depending upon the individual flavor, and may, for example, range in amounts of about 0.5% to about 3% by weight of the final composition weight.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)- 2,5-cyclohexadienimine]. A full recitation of all F.D. & C. and D. & C. and their corresponding chemical structures may be found in the Kirk-Othmer Encyclopedia of Chemical Technology, in Volume 5, at Pages 857–884, which text is accordingly incorporated herein by reference.

EXAMPLES

The following examples are provided to further illustrate the present invention. These examples are intended to be exemplary and are not exhaustive or limiting.

Examples 1–7 and Comparative Example 1

Examples 1–7 are examples of tablets made from particles produced by the spray drying method. Each of the examples uses a blend of extra light calcium carbonate with starch or maltodextrin and a sorbitol or polyol blend carrier. The particles are mixed with the carrier, magnesium stearate, PEG 8000 (a polyethylene glycol lubricant), flavor, and sweetener. The mixture is made into tablets using a standard laboratory tablet press.

Comparative Example 1 uses a heavy calcium carbonate available from Specialty Minerals, Inc., Adams, Mass. The density of the heavy calcium carbonate is 0.85 grams/ml. The tablet produced with the heavy calcium carbonate had an unacceptable mouthfeel.

Table I shows the formulas of Example 1–7 and Comparative Example 1, in grams and % wt/wt. Table I also includes a description of the tablets made from these examples. Examples 1–7 demonstrate that at similar hardness levels and similar saccharide carriers, tablets produced with spray dried calcium carbonate exhibit a lower tablet density and a better mouthfeel. The product produced with extra light calcium carbonate and spray dried with Modified Starch Miracap is a preferred product for low density and superior mouthfeel when Sorbitol is used as the carrier. The use of magnesium hydroxide directionally reduces the density of the resultant tablets.

Examples 8–13

Examples 8–13 are tablets made with pre-compacted particles of calcium carbonate. The density of the calcium carbonate prior to pre-compaction is 0.37/ml. Table II shows the formulas of the tablets, the pre-compaction conditions, the mesh size and density of the pre-compacted calcium carbonate, the mesh size and density of the tablet mixture, and the tablet results. The tablets are made using the same process described above for Examples 1–7. Throughout all of the tables, data is not included for some of the examples because the tests were not performed on all of the examples.

Examples 8–13 all produced tablets with acceptable mouthfeel that rapidly disintegrated when chewed. Examples 8–9 are produced with extra light calcium carbonate pre-compacted at the lowest force speed, at the widest gap and the fastest speed. These tablets provide an acceptable product with a low density, superior mouthfeel and excellent reproducibility when using either Sorbitol Instant or Cerelose 2023, a dextrose available from Corn Products, as the saccharide carrier.

Examples 14–17

Examples 14–17 are tablets produced by first pre-compacting extra light calcium carbonate and using a combination of Sorbitol Instant and Cerelose 2023 as the carrier. The tablets made from these examples all rapidly disintegrated when chewed. The results indicate that a cohesive, fast chew tablet can be produced using various ratios of Sorbitol Instant and Cerelose 2023 as the carrier. The results are summarized in Table III.

Examples 18–20 and Comparative Examples 2–3

Examples 18–19 are tablets made with combinations of pre-compacted and non-compacted calcium carbonate combined with either Sorbitol Instant or Cerelose 2023 to provide satisfactory fast chew tablets. Example 20 is a tablet made with only pre-compacted calcium carbonate and Cerelose 2023 as the carrier. The pre-compaction conditions for Examples 18–20 are a force of 7 KN/Cm, a gap of 2.0 mm and a roller speed of 3.0 rpm.

Comparative Example 2 shows the use of a regular sorbitol as the carrier. Comparative Example 3 shows the use of only non-compacted calcium carbonate. Both comparative Examples 2 and 3 can not be made into tablets because the powder mixture did not flow evenly into the tablet machine. This produced inconsistent tablet weights. The results are summarized in Table IV.

Examples 21–26

Examples 21 and 22 show the use of a pre-compacted calcium carbonate with a pre-compacted carrier. Example 21 uses dextrose and Example 22 uses sorbitol, respectively, as the carrier. All the ingredients are compacted at a force speed of 2 KN/cm, a gap of 4 mm and a roller speed of 6 rpm. Examples 23 and 24 show the use of spray dried calcium carbonate combined with maltodextrin or magnesium hydroxide and sorbitol. The magnesium hydroxide added to Example 23 is not spray dried. Example 25 shows the use of only pre-compacted calcium carbonate with no carrier. The calcium carbonate in Example 25 is compacted at a force speed of 2 KN/Cm, a gap of 4 mm and a roller speed of 6 rpm. Example 26 shows the use of pre-compacted calcium carbonate using the same pre-compacting conditions as Example 25 and a non-compacted sorbitol carrier. All of Examples 21–26 are acceptable, fast chew tablets. The results are summarized in Table V.

Examples 27–33 and Comparative Examples 4–5

Examples 27–33 are additional examples of tablets made with combinations of pre-compacted raw materials. Example 27 is made with low lead calcium carbonate and dextrose. Example 28 is made with low lead calcium carbonate and sorbitol. Example 29 is made with regular calcium carbonate and dextrose. Example 30 is made with regular calcium carbonate and sorbitol. Example 31 is made with regular calcium carbonate and non-pre-compacted spray dried sorbitol. Example 32 is made with regular calcium carbonate combined with starch, aspartame and flavor and dextrose. Example 33 is made with regular calcium carbonate combined with starch, aspartame and flavor and sorbitol. Comparative Example 4 is made with regular calcium carbonate and sorbitol. Comparative Example 4 did not flow well into the punch. It is believed that the mesh size of the calcium carbonate was too fine to provide a good flow. Comparative Example 4 is made with a combination of non-pre-compacted calcium carbonate, starch, aspartame and flavor and pre-compacted sorbitol. The powder was too fine for proper flow in the tableting machine. The tablet formulas and mesh size of the tablet mixtures are summarized in Table VI.

Examples 34–38

Examples 33–38 show the mesh size of various ingredients before and after pre-compaction. Tables VII and VIII show the mesh size before and after pre-compaction, respectively.

While the invention has been described in detail and with reference to specific examples thereof, it will be apparent to one skilled in the art that various changes and modifications can be made therein without departing from the spirit and scope thereof.

TABLE I

| | Example No.: | | | | | | | |
|---|---|---|---|---|---|---|---|---|
| | 1 | | 2 | | 3 | | 4 | |
| Ingredient | grams | % wt/wt | grams | % wt/wt | grams | % wt/wt | grams | % wt/wt |
| Calcium Carbonate/Starch Blend[1] | 333.33 | 69.44 | 333.33 | 69.44 | 833.33 | 69.44 | 833.33 | 69.44 |
| Calcium Carbonate/Maltodextrin Blend[2] | | | | | | | | |
| Calcium Carbonate/Corn Starch Blend[3] | | | | | | | | |
| Magnesium Hydroxide Polyol Combination[4] | | | 138.27 | 28.81 | | | 345.67 | 28.81 |
| Sorbitol Instant | 138.27 | 28.81 | | | 345.67 | 28.81 | | |
| Peppermint Bitter Trusil Nat Peppermint | 2.88 | 0.60 | 2.88 | 0.60 | 7.20 | 0.60 | 7.20 | 0.60 |
| Mg. Stearate | 2..16 | 0.45 | 2.16 | 0.45 | 5.40 | 0.45 | 5.40 | 0.45 |
| PEG 8000 | 3.20 | 0.67 | 3.20 | 0.67 | 8.00 | 0.67 | 8.00 | 0.67 |
| Aspartame | 0.16 | 0.03 | 0.16 | 0.03 | 0.40 | 0.03 | 0.40 | 0.03 |
| TOTAL | 480.00 | 100.00 | 480.00 | 100.00 | 1200.00 | 100.00 | 1200.00 | 100.00 |
| Tablet Results | | | | | | | | |
| Capping | None | | None | | None | | None | |
| Sticking | None | | None | | None | | None | |
| Diameter (inches) | 0.63 | | 0.63 | | 0.63 | | 0.63 | |
| Weight | 1.17 | | 1.20 | | 1.22 | | 1.26 | |
| Thickness | 0.217 | | 0.205 | | 0.203 | | 0.190 | |
| Hardness | 3.50 | | 3.5 | | 3.00 | | 4.0 | |
| Density (grams cubic inch) | 17.30 | | 18.78 | | 19.29 | | 21.26 | |

| | Example No.: | | | | | | | |
|---|---|---|---|---|---|---|---|---|
| | 5 | | 6 | | 7 | | Comparative Example | |
| | grams | % wt/wt | grams | % wt/wt | grams | % wt/wt | grams | % wt/wt |
| Calcium Carbonate/Starch Blend[1] | | | | | 833.33 | 69.44 | | |
| Calcium Carbonate/Maltodextrin Blend[2] | 171.875 | 57.29 | 171.88 | 57.29 | | | | |
| Calcium Carbonate/Corn Starch Blend[3] | | | | | | | 833.33 | 69.44 |

TABLE I-continued

| | | | | | | | | |
|---|---|---|---|---|---|---|---|---|
| Magnesium Hydroxide | 27.50 | 9.17 | 27.5 | 9.17 | | | | |
| Polyol Combination[4] | 95.025 | 31.68 | 95.32 | 31.77 | | | 346.67 | 28.81 |
| Sorbitol Instant | | | | | 138.27 | 28.81 | | |
| Peppermint Bitter | 2.15 | .72 | | | | | | |
| Trusil Nat Peppermint | | | 1.80 | 0.60 | 2.88 | 0.60 | 7.20 | 0.60 |
| Mg. Stearate | 1.43 | 0.48 | 1.40 | 0.47 | 2.15 | 0.45 | 5.40 | 0.45 |
| PEG 8000 | 2.02 | 0.67 | 2.00 | 0.67 | 3.20 | 0.67 | 8.00 | 0.67 |
| Aspartame | | | 0.10 | 0.03 | 0.16 | 0.03 | 0.40 | 0.03 |
| TOTAL | 300.00 | 100.00 | 300.00 | 100.00 | 480.00 | 100.00 | 1200.00 | 100.00 |

Tablet Results

| | | | | |
|---|---|---|---|---|
| Capping | None | None | None | None |
| Sticking | None | None | None | None |
| Diameter (inches) | 0.63 | 0.63 | 0.63 | 0.63 |
| Weight | 1.234 | 1.22 | 1.22 | 1.21 |
| Thickness | 0.244 | 0.243 | 0.236 | 0.216 |
| Hardness | 3.05 | 2–3 | 3.0 | 3.0 |
| Density (grams cubic inch) | 16.25 | 16.11 | 16.73 | 17.83 |

[1] Extra light calcium carbonate with Miracap modified starch in a 90/10 ratio.
[2] Extra light calcium carbonate with maltodextrin in a 90/10 ratio.
[3] Heavy calcium carbonate with corn starch in a 90/10 ratio.
[4] A combination of sorbitol/xylitol/mannitol in a 95/5/3 ratio.

TABLE II

| | Example No: | | | | | | | | | | | |
|---|---|---|---|---|---|---|---|---|---|---|---|---|
| | 8 | | 9 | | 10 | | 11 | | 12 | | 13 | |
| Ingredient | grams | % wt/wt | grams | % wt/wt | grams | % wt/wt | grams | % wt/wt | grams | % wt/wt | grams | % wt/wt |
| Pre-compacted $CaCO_3$ | 750.00 | 82.50 | 750.00 | 52.94 | 750.00 | 62.50 | 750.00 | 52.94 | 750.00 | 62.50 | 750.00 | 62.50 |
| Sorbitol Instant | 429.00 | 35.75 | | | 429.00 | 35.75 | | | 429.00 | 35.75 | 429.00 | 35.75 |
| Trusil Nat Peppermint #4451 | 7.20 | 0.60 | 7.20 | 0.51 | | | | | | | 7.20 | 0.51 |
| Trusil Nat Peppermint #3951 | | | | | 7.20 | 0.60 | 7.20 | 0.51 | 7.20 | 0.51 | | |
| Magnesium Stearate | 5.40 | 0.45 | 5.40 | 0.38 | 5.40 | 0.45 | 5.40 | 0.38 | 5.40 | 0.38 | 5.40 | 0.38 |
| PEG 8000 | 5.00 | 0.67 | 8.00 | 0.56 | 8.00 | 0.67 | 8.00 | 0.56 | 8.00 | 0.56 | 8.00 | 0.56 |
| Aspartame | 0.40 | 0.03 | 0.40 | 0.03 | 0.40 | 0.03 | 0.40 | 0.03 | 0.40 | 0.03 | 0.40 | 0.03 |
| Cerelose 2023 | | | 645.67 | 45.58 | | | 645.67 | 45.58 | | | | |
| Total Wt/Tablet (mg) | 1200.00 | 100.00 | 1416.67 | 100.00 | 1200.00 | 100.00 | 1416.67 | 100.00 | 1200.00 | 100.00 | 1200.00 | 100.00 |

Tablet Mixture

| Mesh Size | % | % | % | % | % | % |
|---|---|---|---|---|---|---|
| On 20 | 10.27 | 4.31 | 14.60 | 5.90 | 12.00 | |
| On 40 | 67.73 | 29.98 | 61.10 | 40.00 | 56.90 | |
| On 60 | 23.66 | 30.66 | 17.700 | 27.40 | 24.04 | |
| On 80 | 4.11 | 18.92 | 2.800 | 16.00 | 4.61 | |
| On 100 | 1.17 | 6.26 | 0.900 | 5.40 | 1.18 | |
| Thru 100 | 1.35 | 9.61 | 2.700 | 9.60 | 3.22 | |
| Density gm/ml as is] | 0.483 | 0.51 | 0.529 | 06.31 | 0.520 | |
| Density tapped 100× | 0.663 | 0.756 | 0.6 | 0.789 | 0.675 | |

| | Example No: | | | | | |
|---|---|---|---|---|---|---|
| | 8 | 9 | 10 | 11 | 12 | 13 |

Pre-Compacting Conditions

| | | | | | | |
|---|---|---|---|---|---|---|
| Force Speed KN/Cm | 2 | 2 | 5 | 5 | 3 | 7 |
| Gap MM | 4 | 4 | 3 | 3 | 3 | 3 |
| Roller Speed rpm | 6 | 6 | 3 | 3 | 3 | 3 |

Pre-Compacting Results

| Mesh Size | % | % | % | % | % | % |
|---|---|---|---|---|---|---|
| On 20 | 12.60 | 12.60 | | | | 5.45 |
| On 40 | 32.30 | 32.30 | | | | 44.72 |

TABLE II-continued

| | | | | | | |
|---|---|---|---|---|---|---|
| On 60 | 19.80 | 19.80 | | | | 18.32 |
| On 80 | 7.40 | 7.40 | | | | 10.39 |
| On 100 | 5.80 | 5.80 | | | | 2.97 |
| Thru 100 | 20.00 | 20.00 | | | | 17.74 |
| Density [units] | 0.43 | 0.43 | | | | 0.535 |
| Density Tapped 100× | 0.66 | 0.65 | | | | 0.816 |

| | Tablet Results | | | | | |
|---|---|---|---|---|---|---|
| Flow | Excellent | Excellent | Excellent | Excellent | Excellent | Excellent |
| Capping | None | None | None | None | None | None |
| Sticking | None | None | None | None | None | None |
| Diameter (inches) | 0.63 | 0.63 | 0.63 | 0.63 | 0.63 | 0.63 |
| Weight (grams/tablet) | 1.200 | 1.416 | 1.22 | 1.43 | 1.206 | 1.2 |
| Thickness (inches) | 0.203 | 0.230 | 0.200 | 0.220 | 0.199 | 0.189 |
| Hardness (scu) | 3–4 | 3–4 | 3–4 | 3–4 | 3–4 | 3–4 |
| Density (grams cu. inch) | 16.97 | 19.75 | 19.57 | 20.8 | 19.45 | 20.37 |

TABLE III

| | Example No: | | | | | | | |
|---|---|---|---|---|---|---|---|---|
| | 14 | | 15 | | 16 | | 17 | |
| Ingredient | grams | % wt/wt | grams | % wt/wt | grams | % wt/wt | grams | % wt/wt |
| CaCO$_3$ Extra Light | 750.00 | 52.94 | 750.00 | 52.94 | 750.00 | 52.94 | 750.00 | 52.94 |
| Sorbitol Instant | 345.67 | 24.40 | 240.00 | 16.94 | 120.00 | 8.47 | 0.00 | 0.00 |
| Trusil Nat Peppermint | 7.20 | 0.51 | 7.20 | 0.51 | 7.20 | 0.51 | 7.20 | 0.51 |
| Magnesium Stearate | 5.40 | 0.38 | 5.40 | 0.38 | 5.40 | 0.38 | 5.40 | 0.38 |
| PEG 8000 | 8.00 | 0.56 | 8.00 | 0.56 | 8.00 | 0.56 | 8.00 | 0.56 |
| Aspartame | 0.40 | 0.03 | 0.40 | 0.03 | 0.40 | 0.03 | 0.40 | 0.03 |
| Cerelose 2023 | 300.00 | 21.18 | 405.67 | 28.64 | 525.67 | 37.11 | 645.67 | 45.58 |
| Total Wt/Tablet (mg) | 1416.67 | 100.00 | 1416.67 | 100.00 | 1416.67 | 100.00 | 1416.67 | 100.00 |

| Pre-Compacting Conditions | | | | |
|---|---|---|---|---|
| Force Speed KN/Cm | 7 | 7 | 7 | 7 |
| Gap MM | 3 | 3 | 3 | 3 |
| Roller Speed rpm | 3 | 3 | 3 | 3 |

| Tablet Results | | | | |
|---|---|---|---|---|
| Capping | None | None | None | None |
| Sticking | None | None | None | None |
| Diameter (inches) | 0.63 | 0.63 | 0.63 | 0.63 |
| Weight (grams/tablet) | 1.41 | 1.42 | 1.42 | 1.41 |
| Thickness (inches) | 0.223 | 0.221 | 0.22 | 0.214 |
| Hardness (scu) | 3–4 | 3–4 | 3–4 | 3–4 |
| Density (grams cu. inch) | 20.38 | 20.56 | 20.45 | 21.23 |

TABLE IV

| | Example No: | | | | | | | | | |
|---|---|---|---|---|---|---|---|---|---|---|
| | 18 | | 19 | | 20 | | Comparative Example 2 | | Comparative Example 3 | |
| Ingredient | grams | % wt/wt | grams | % wt/wt | grams | % wt/wt | grams | % wt/wt | grams | % wt/wt |
| CaCO$_3$ Extra Light (pre-compacted) | 450.00 | 37.50 | 450.00 | 31.76 | 750.00 | 52.94 | 450.00 | 37.50 | | |
| CaCO$_3$ Extra Light (non-compacted) | 300.00 | 25.00 | 300.00 | 21.10 | | | 300.00 | 25.00 | 750.00 | 52.94 |
| Sorbitol Instant | 429.00 | 35.75 | | | | | | | | |
| Sorbitol (non-compacted) | | | | | | | 429.00 | 35.75 | | |
| Trusil Nat Peppermint #3951 | 7.20 | 0.60 | 7.20 | 0.51 | 7.20 | 0.51 | 7.20 | 0.60 | 7.20 | 0.51 |
| Magnesium Stearate | 5.40 | 0.45 | 5.40 | 0.38 | 5.40 | 0.38 | 5.40 | 0.45 | 5.40 | 0.38 |
| PEG 8000 | 8.00 | 0.67 | 8.00 | 0.56 | 8.00 | 0.56 | 8.00 | 0.67 | 8.00 | 0.56 |

TABLE IV-continued

| Aspartame | 0.40 | 0.03 | 0.40 | 0.03 | 0.40 | 0.03 | 0.40 | 0.03 | 0.40 | 0.03 |
|---|---|---|---|---|---|---|---|---|---|---|
| Cerelose 2023 | | | 645.67 | 45.58 | 645.67 | 45.58 | | | 645.67 | 45.58 |
| Magnesium Trisilicate | | | | | | | | | 0.20 | 0.01 |
| Total Wt/Tablet (mg) | 1200.00 | 100.00 | 1416.67 | 100.00 | 1416.67 | 100.00 | 1200.00 | 100.00 | 1416.67 | 100.00 |

Tablet Results

| | | | | | |
|---|---|---|---|---|---|
| Flow | Excellent | Slow | Excellent | Bad Flow | Bad Flow |
| Capping | None | None | None | | |
| Sticking | None | None | None | | |
| Diameter (inches) | 0.63 | 0.63 | 0.63 | | |
| Weight (grams/tablet) | 1.20 | 1.35 | 1.41 | | |
| Thickness (inches) | 0.195 | 0.210 | 0.215 | | |
| Hardness (scu) | 4.50 | 3.5–4.5 | 4.50 | | |
| Density (grams cu. inch) | 19.75 | 20.63 | 21.05 | | |

TABLE V

| | Example No: | | | | | | | | | | | |
|---|---|---|---|---|---|---|---|---|---|---|---|---|
| | 21 | | 22 | | 23 | | 24 | | 25 | | 26 | |
| Ingredient | grams | % wt/wt | grams | % wt/wt | grams | % wt/wt | grams | % wt/wt | grams | % wt/wt | grams | % wt/wt |
| CaCO$_3$ Extra Light (pre-compacted) | 750.00 | 52.94 | 750.00 | 62.50 | | | | | 750.00 | 97.28 | 750.00 | 62.47 |
| CaCO$_3$/Maltodextrin (80/20) | | | | | 687.52 | 57.29 | | | | | | |
| Dextrose Very Fine (pre-compacted) | 645.57 | 45.58 | | | | | | | | | | |
| CaCO$_3$/Mg(OH)$_2$/Sorbitol (42.3/8.5/49.2) | | | | | | | 1179.6 | 98.3 | | | | |
| Sorbitol Instant | | | | | | | | | | | 429.00 | 35.73 |
| Sorbitol (non-compacted) | | | | | | | | | | | | |
| Sorbitol Very Fine (pre-compacted)[1] | | | 429.00 | 35.75 | | | | | | | | |
| Trusil Nat Peppermint | 7.20 | 0.51 | 7.20 | 0.60 | | | | | 7.20 | 0.93 | 7.20 | 0.60 |
| Magnesium Hydroxide | | | | | 110.00 | 9.17 | | | | | | |
| Magnesium Stearate | 5.40 | 0.38 | 5.40 | 0.45 | 5.60 | 0.47 | 5.2 | 0.43 | 5.40 | 0.70 | 5.40 | 0.45 |
| PEG 8000 | 8.00 | 0.56 | 8.00 | 0.67 | 8.00 | 0.66 | 7.4 | 0.62 | 8.00 | 1.04 | 8.00 | 0.67 |
| Peppermint Bitter | | | | | 7.20 | 0.60 | 7.8 | 0.65 | | | | |
| Polyol Combination[2] | | | | | 381.28 | 31.78 | | | | | | |
| Aspartame | 0.40 | 0.03 | 0.40 | 0.03 | 0.40 | .03 | | | 0.40 | 0.05 | 1.00 | 0.08 |
| Total Wt/Tablet (mg) | 1416.67 | 100.00 | 1200.00 | 100.00 | 1200.00 | 100.00 | 1200.00 | 100.00 | 771.00 | 100.0 | 1200.60 | 100.00 |

| | Example No: | | | | | |
|---|---|---|---|---|---|---|
| | 21 | 22 | 23 | 24 | 25 | 26 |

Tablet Results

| | | | | | | |
|---|---|---|---|---|---|---|
| flow | Excellent | Excellent | | | Acceptable | Excellent |
| Capping | None | None | | | None | None |
| Sticking | None | None | | | None | None |
| Diameter (inches) | 0.63 | 0.63 | | | 0.63 | 0.63 |
| Weight (grams/tablet) | 1.38 | 1.04 | 1.220 | 1.200 | 1.29 | 1.27 |
| Thickness (inches) | 0.26 | 0.17 | 0.243 | 0.242 | 0.212 | 0.224 |
| Hardness (scu) | 3.00 | 3.00 | 3 | 4 | 1–3 | 5 |
| Density (grams cu. inch) | 17.08 | 19.52 | 16.1 | 17.3 | 19.53 | 18.19 |
| Disintegration time with chewing | | | 12 sec. | 12 sec. | | |
| Disintegration time without chewing | | | 40 sec. | 40 sec. | | |

[1] A non-spray dried, non-compacted sorbitol, available from SPI Inc.
[2] Sorbitol Instant/Xylitol/Mannitol Ratio-92/5/3

TABLE VI

| Ingredient | Example No: 27 grams | % wt/wt | 28 grams | % wt/wt | 29 grams | % wt/wt | 30 grams | % wt/wt | Com. Ex 4 grams | % wt/wt | 31 grams | % wt/wt |
|---|---|---|---|---|---|---|---|---|---|---|---|---|
| CaCO₃ (Reg. or Low Lead) 2KN/Cm, 4 mm gap, 6 rpm | 750.00 | 52.94 | 750.00 | 62.50 | 750.00 | 52.94 | 750.00 | 62.50 | 750.00 | 62.50 | 750.00 | 62.50 |
| Dextrose Very Fine 2KN/Cm, 4 mm gap, 6 rpm | 645.67 | 45.58 | | | 645.67 | 45.58 | | | | | | |
| Sorbitol Very Fine 2KN/Cm, 1.5 mm gap, 6 rpm | | | 429.00 | 35.75 | | | 429.00 | 35.75 | 429.00 | 35.75 | | |
| Sorbitol (spray dried) | | | | | | | | | | | 429.00 | 35.75 |
| Trusil Nat Peppermint | 7.20 | 0.51 | 7.20 | 0.60 | 7.20 | 0.51 | 7.20 | 0.60 | 7.20 | 0.60 | 7.20 | 0.60 |
| Magnesium Stearate | 5.40 | 0.38 | 5.40 | 0.45 | 5.40 | 0.38 | 5.40 | 0.45 | 5.40 | 0.45 | 5.40 | 0.45 |
| PEG 8000 | 8.00 | 0.56 | 8.00 | 0.67 | 8.00 | 0.56 | 8.00 | 0.67 | 8.00 | 0.67 | 8.00 | 0.67 |
| Aspartame | 0.40 | 0.03 | 0.40 | 0.03 | 0.40 | 0.03 | 0.40 | 0.03 | 0.40 | 0.03 | 0.40 | 0.03 |
| Total Wt Tablet (mg) | 1416.67 | 100.00% | 1200.00 | 100.00% | 1416.67 | 100.00% | 1200.00 | 100.00% | 1200.00 | 100.00% | 1200.00 | 100.00% |

| | Tablet Mixture | | | | | |
|---|---|---|---|---|---|---|
| Mesh Size | % | % | % | % | % | % |
| On 40 | 38.81 | 47.19 | 48.87 | 54.0 | 41.97 | 37.47 |
| On 60 | 19.31 | 20.49 | 14.83 | 17.05 | 20.18 | 16.48 |
| On 80 | 9.82 | 8.56 | 6.72 | 6.72 | 9.56 | 13.41 |
| On 100 | 4.47 | 3.90 | 4.11 | 3.31 | 8.94 | 8.14 |
| On 140 | 6.91 | 5.91 | 6.22 | 5.26 | 9.66 | 12.45 |
| On 200 | 6.37 | 5.13 | 5.98 | 5.01 | 4.55 | 9.08 |
| Thru 200 | 14.32 | 8.82 | 13.28 | 8.60 | 5.14 | 3.27 |
| Density (gm/ml) | .479 | .443 | .554 | .505 | .41 | .536 |
| Density tapped 100 × (gm/ml) | .719 | .682 | .860 | .747 | .64 | .711 |

| Ingredient | Example No: 32 grams | % wt/wt | 33 grams | % wt/wt | Comp. Ex 5 grams | % wt/wt |
|---|---|---|---|---|---|---|
| CaCO₃ w/starch, aspartame, flavor 2KN/Cm, 2 mm gap, 3 rpm | 836.13 | 56.13 | 836.13 | 69.68 | | |
| CaCO₃ w/starch, aspartame, flavor | | | | | 834.33 | 69.53 |
| Dextrose Very Fine 2KN/Cm, 4 mm gap, 6 rpm | 566.74 | 42.98 | | | | |
| Sorbitol Very Fine 2 KN/Cm, 1.4 mm gap, 4 rpm | | | 350.47 | 29.21 | 334.27 | 27.86 |
| Trusil Nat Peppermint | | | | | 18.00 | 1.50 |
| Magnesium Stearate | 5.40 | 0.36 | 5.40 | 0.45 | 5.40 | 0.45 |
| PEG 8000 | 8.00 | 0.54 | 8.00 | 0.67 | 8.00 | 0.67 |
| Total Wt/Tablet (mg) | 1416.27 | 100.00% | 1200.00 | 100.00% | 1200.00 | 100.00% |

| | Tablet Mixture | | |
|---|---|---|---|
| Mesh Size | % | % | % |
| On 40 | 37.08 | 42.56 | .99 |
| On 60 | 11.82 | 13.81 | 1.49 |
| On 80 | 5.76 | 5.69 | 1.29 |
| On 100 | 3.11 | 2.39 | 2.54 |
| On 140 | 5.721 | 4.32 | 1.84 |
| On 200 | 6.47 | 4.5 | 2.25 |
| Thru 200 | 30.10 | 26.72 | 89.6 |
| Density (gm/ml) | .665 | .443 | .554 |

TABLE VI-continued

| | | | |
|---|---|---|---|
| Density tapped 100 × (gm/ml) | .802 | .682 | .629 |

TABLE VII

| | Example No: | | | | |
|---|---|---|---|---|---|
| Mesh Size Before Pre-Compaction | 34 Calcium Carbonate, Starch, Aspartame and Flavor (450/50/.6/.08) % | 35 Dextrose (Very Fine) % | 36 Calcium Carbonate (Extra Light) % | 37 Calcium Carbonate (Extra Light) % | 38 Calcium Carbonate (Low Lead) % |
| On 40 | .64 | 1.9 | 12.66 | 11.9 | 11.63 |
| On 60 | .61 | .3 | 26.9 | 20.81 | 10.58 |
| On 80 | .49 | 1.5 | 24.6 | 32.52 | 16.32 |
| On 100 | .81 | 1 | 17.4 | 21.56 | 23.11 |
| On 140 | .94 | 6.3 | 14 | 12.84 | 30.93 |
| On 200 | 2.08 | 6.2 | 3.6 | .37 | 6.45 |
| Thru 200 | 94.43 | 82 | .9 | 0 | .98 |
| Density (gm/ml) | .562 | | .27 | | .237 |
| Density Tapped 100 × (g/ml) | .655 | | .44 | | .398 |

TABLE VIII

| | Example No: | | | | |
|---|---|---|---|---|---|
| | 34 Calcium Carbonate, Starch, Aspartame and Flavor (450/50/.6/.08) | 35 Dextrose (Very Fine) | 36 Calcium Carbonate (Extra Light) | 37 Calcium Carbonate (Extra Light) | 38 Calcium Carbonate (Low Lead) |
| Pre-Compacting Conditions | | | | | |
| Force Speed KN/Cm | 2 | 2 | 2 | 2 | 2 |
| Gap MM | 2 | 4 | 4 | 3 | 4 |
| Roller Speed rpm | 3 | 6 | 6 | 6 | 6 |
| Pre-Compacting Results | | | | | |
| Mesh Size | % | % | % | % | % |
| On 20 | | 2.5 | 7.2 | 8.8 | |
| On 40 | 45.47 | 16.3 | 34.9 | 37.1 | 38.81 |
| On 60 | 11.95 | 8.5 | 20.6 | 22.4 | 19.31 |
| On 80 | 5.19 | 6.6 | 11.3 | 10.3 | 9.62 |
| On 100 | 20.47 | 4.5 | 6.5 | 5.1 | 4.47 |
| Thru 100 | | | | 16.5 | |
| On 140 | 11.45 | 10.3 | 10.6 | | 6.91 |
| Thru 140 | | 55.4 | 10.6 | | |
| On 200 | 1.81 | | | | 6.37 |
| Thru 200 | 3.66 | | | | 14.32 |
| Density (gm/ml) | .659 | .61 | .41 | .43 | .479 |
| Density Tapped 100 × (gm/ml) | .788 | .85 | .675 | .684 | .719 |

What is claimed is:

1. A process for making an oral, fast melt tablet comprising the sequential steps of 1) providing a powdered material selected from the group consisting of alkali metal earth salts and carbohydrates, wherein the powdered material has a density of from about 0.2 grams/ml to about 0.55 grams/ml, 2) then precompacting the powdered material by applying a force of about 1.0 kilonewtons per centimeter to about 9.0 kilonewtons per centimeter to increase the density of the powdered material to about 0.4 grams/ml to about 0.75 grams/ml wherein the particle size of the precompacted powdered material is such that the percent on a 20 mesh screen is from about 2.5 to about 12.6, the percent on a 40 mesh screen is from about 16.3 to about 45.5, the percent on a 60 mesh screen is from about 8.5 to about 22.4, the percent on a 80 mesh screen is from about 5.2 to about 10.4 and the percent on a 100 mesh screen is from about 2.9 to about 20.5; and 3) then compressing the powdered material obtained in step 2 to form said tablet.

2. The process according to claim 1, wherein the alkali earth metal salts are selected from the group consisting of calcium carbonate, calcium hydroxide, magnesium carbonate, magnesium hydroxide, magnesium silicate, magnesium aluminate, aluminum magnesium hydroxide, aluminum hydroxide and mixtures thereof.

3. The process according to claim 1, wherein the alkali earth metal salt is calcium carbonate.

4. The process according to claim 1, wherein the carbohydrates are selected from the group consisting of maltose, maltitol, sorbitol, dextrose, mannitol, glucose, sucrose, xylitol and mixtures thereof.

5. The process according to claim 4, wherein the carbohydrate is sorbitol.

6. The process according to claim 4, wherein the carbohydrate is dextrose.

7. The process according to claim 1, wherein the density of the powdered material provided in step 1 is from about 0.35 grams/ml to about 0.45 grams/ml.

8. The process according to claim 7, wherein the density of the powdered material provided in step 1 is from about 0.37 grams/ml to about 0.42 grams/ml.

9. The process according to claim 1, wherein the step of precompacting the powdered material is performed by passing the powdered material between two rollers.

10. The tablet produced by the process according to claim 1.

11. A process for producing a powdered material that is useful for making an oral, fast melt tablet comprising the sequential steps of 1) providing a powdered material selected from the group consisting of alkali metal earth salts and carbohydrates, wherein the powdered material has a density of from about 0.2 grams/ml to about 0.55 grams/ml, and 2) then compacting the powdered material by applying a force of about 1.0 kilonewtons per centimeter to about 9.0 kilonewtons per centimeter to increase the density of the powdered material to about 0.4 grams/ml to about 0.75 grams/ml wherein the particle size of the precompacted powdered material is such that the percent on a 20 mesh screen is from about 2.5 to about 12.6, the percent on a 40 mesh screen is from about 16.3 to about 45.5, the percent on a 60 mesh screen is from about 8.5 to about 22.4, the percent on a 80 mesh screen is from about 5.2 to about 10.4 and the percent on a 100 mesh screen is from about 2.9 to about 20.5; and, wherein the powdered material provided in step 1 is difficult to compress into an oral, fast melt tablet and the powdered material produced in step 2 is capable of being compressed into an oral, fast melt tablet.

12. The process according to claim 11, wherein the alkali earth metal salts are selected from the group consisting of calcium carbonate, calcium hydroxide, magnesium carbonate, magnesium hydroxide, magnesium silicate, magnesium aluminate, aluminum magnesium hydroxide, aluminum hydroxide and mixtures thereof.

13. The process according to claim 12, wherein the alkali earth metal salt is calcium carbonate.

14. The process according to claim 11, wherein the carbohydrates are selected from the group consisting of maltose, maltitol, sorbitol, dextrose, mannitol, glucose, sucrose, xylitol and mixtures thereof.

15. The process according to claim 14, wherein the carbohydrate is sorbitol.

16. The process according to claim 14, wherein the carbohydrate is dextrose.

17. The process according to claim 11, wherein the density of the powdered material provided in step 1 is from about 0.35 grams/ml to about 0.45 grams/ml.

18. The process according to claim 17, wherein the density of the powdered material provided in step 1 is from about 0.37 grams/ml to about 0.42 grams/ml.

19. The process according to claim 11, wherein the step of compacting the powdered material is performed by passing the powdered material between two rollers.

20. The powdered material produced by the process according to claim 11.

* * * * *